United States Patent
Yang et al.

(10) Patent No.: US 6,623,760 B1
(45) Date of Patent: Sep. 23, 2003

(54) METHOD OF PREPARING PARTICLES FOR AGGLOMERATION

(75) Inventors: Tsong-Toh Yang, Warren, NJ (US); Stephen K. C. Yu, Somerville, NJ (US); Charles G. Eckhart, Scotch Plains, NJ (US); Michael B. Mitchell, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/490,796

(22) Filed: Jan. 26, 2000

Related U.S. Application Data

(60) Provisional application No. 60/117,654, filed on Jan. 28, 1999.

(51) Int. Cl.$^7$ .................................................. A61K 9/14
(52) U.S. Cl. ........................ 424/489; 424/499; 424/422; 424/434
(58) Field of Search .................................. 424/493, 489, 424/499, 422, 434; 514/826

(56) References Cited

U.S. PATENT DOCUMENTS

| | | | | |
|---|---|---|---|---|
| 4,161,516 A | | 7/1979 | Bell | 424/14 |
| 5,709,884 A | * | 1/1998 | Trofast et al. | 424/489 |
| 6,030,604 A | * | 2/2000 | Trofast | 424/46 |

FOREIGN PATENT DOCUMENTS

| | | |
|---|---|---|
| EP | 0 508 969 A1 | 10/1992 |
| GB | 1 520 247 | 8/1978 |
| WO | WO 92/18110 | 10/1992 |
| WO | WO 95/05805 | 3/1995 |
| WO | WO 95/09616 | 4/1995 |
| WO | WO 98/41193 | 9/1998 |
| WO | WO 99/54048 | 10/1999 |

OTHER PUBLICATIONS

L–E. Briggner et al., "The Use of Isothermal Microcalorimetry in the Study of Changes in Crystallinity Induced During the Processing of Powders," *International Journal of Pharmaceutics*, vol. 105, pp. 125–135 (1994).

T. Sebhatu et al., "Effect of Moisture Sorption on Tabletting Characteristics of Spray Dried (15% Amorphous) Lactose," *Pharmaceutical Research*, vol. 11, pp. 1233–1238 (1994).

* cited by examiner

*Primary Examiner*—Thurman K. Page
*Assistant Examiner*—Liliana Di Nola Baron
(74) *Attorney, Agent, or Firm*—Robert A. Franks

(57) ABSTRACT

Methods of preparing particulates for agglomeration, having a specified particle size distribution and desired convertible amorphous content, are described. The method involves a plurality of micronizing steps at least two of which are separated by a curing step. In the curing step, a stimulus such as humidity may be used to crystallize at least some, and in many instances preferably all, of the convertible amorphous content.

22 Claims, No Drawings

METHOD OF PREPARING PARTICLES FOR AGGLOMERATION

CROSS-REFERENCE TO RELATED APPLICATION

This application claims the benefits under 35 U.S.C. §119(e) from provisional application Ser. No. 60/117,654 filed on Jan. 28, 1999.

FIELD OF THE INVENTION

The present invention relates broadly to the formation of agglomerates, to particulate solid carriers, and/or binders, and/or pharmaceutically active materials for use in the formation of agglomerates, and to methods of forming same and agglomerates so produced. More specifically, the present invention relates to the field of pharmaceutical dosage form design and, in particular, the production of unique solid carriers and/or pharmaceutically active materials and agglomerated dosage forms for administration of pharmaceutically active materials to patients.

INTRODUCTION TO THE INVENTION

There are several known methods of treating diseases and conditions of the upper and lower airway passages and the lungs. These conditions include, for example, asthma and rhinitis. One such technique involves administering certain pharmacologically active agents or drugs such as, for example, mometasone furoate, topically to the airway passages or lungs in an immediately useable form. Mometasone furoate is a topically effective, steroidal anti-inflammatory.

Oral inhalation therapy is one method of delivering such topically active drugs. This form of drug delivery involves the oral administration of a dry powdered drug directly to the afflicted area in a form which is readily available for immediate benefit.

However, inhalation therapy is a particularly demanding dosing system and it involves its own set of unique design and performance problems. Among those problems is a concern over the accuracy and repeatability of dosing. One must try to ensure that the same amount of drug is administered each and every time. Moreover, unlike pills, capsules and creams, oral inhalation therapy must concern itself with not only the dosage form itself, but also a drug delivery device and the interaction between them. One has only to consider over-the-counter nasal sprays to understand this problem. When one squeezes a conventional spray bottle, it is difficult to apply the same amount of force each and every time. With even a slight difference in force, differences in the amount of drug administered can result. Even with somewhat more consistent pump style spray applicators, variations in dosing can occur. While such variation is usually not a problem when administering OTC nasal sprays, variation should be minimized where possible when administering potent prescription medications for such serious conditions as asthma. The dangers of over-medicating or under-medicating and the consequences of such unwanted deviation can be profound. The problem becomes even more complex when the size of the doses are as small as they often are in oral inhalation therapy.

To help mitigate these problems, companies such as Schering Corporation have developed complex and highly accurate inhaler systems for administering powdered medications such as those described in PCT International Publication WO 94/14492, the text of which is hereby incorporated by reference. Such inhaler systems were designed to meter out an exact dose of a powdered medication using a dosing hole of a specific size. The hole is completely filled with drug prior to administration and the entire contents of the dosing hole are then delivered to the patient through a nozzle. The dosing hole is then filled again for the next dose. These devices have been specifically designed to remove, as much as possible, human error and mechanically induced variability in dosing.

While such devices represent a significant advance in oral inhalation therapy, there are still some circumstances in which problems may remain. These problems often center on the properties of the pharmacologically active agent and their interaction with the inhaler. For example, certain drugs are not "free-flowing" and that may make it difficult to move the drug from storage in a reservoir, to measurement in a dosing hole, to delivery from the inhaler. Other drugs may suffer from electrostatic charge problems or may exhibit an unacceptable degree of cohesive force. Such drugs may be "sticky," even when in powdered form. These drugs may clog the inhaler/applicator, affecting its ability to properly meter the intended amount of medication. Such powders may also adhere to the nozzle of the applicator, thus reducing the amount of medication actually delivered. This is often referred to as "hang up." Drugs may also be "fluffy" which makes handling and loading sufficient drug into a dosing hole a real challenge. To make matters even worse, these and other physical properties of various pharmacologically active agents may vary within a single batch of material. This can defeat attempts to compensate.

Related problems may also result based upon the small size of the particles which are generally used in inhalation therapy. Inhalation therapy commonly involves drug particles which are on the order of 10 microns or below. This ensures adequate penetration of the medicament into the lungs of the patient as well as good topical coverage. In order to provide adequate dispensing of such medicines, tight control must be maintained on the size of the particles of the drug. However, powders of this size can be extremely difficult to work with, particularly when small dosages are required. Such powders are typically not free-flowing and are usually light, dusty or fluffy in character, creating problems during handling, processing, and storing. In addition, it can be difficult to repeatedly and accurately load such materials into the dosing hole of an inhaler. Thus not only the properties of the drug, but also the required size of the therapeutic particulate, can combine to cause considerable problems in terms of handling and dosing.

One method of improving the ability to administer fine powdered medicaments is by the inclusion of dry excipients such as, for example, powdered lactose. However, it has been determined that when particularly small doses of medication are required, such as under about 100–500 $\mu$g of drug, the inclusion of conventional excipients may not adequately compensate for the problems associated with the use of fine drug particles. In addition, dry excipients as commonly used generally have particle sizes which are significantly larger than the particle size of the drug. Unfortunately, the use of such large particles can have a significant impact on the amount of drug delivered from dose to dose. Moreover, the intended benefits of the use of such excipients begins to diminish as the size of the dose decreases. Therefore, particle retention within the metering device or the inhalation nozzle and other handling issues can become a serious problem.

Alternatively, drug products can be processed to form agglomerates or pellets which are generally more free-flowing and bulky. One method of agglomerating drugs is described in PCT International Publication WO 95/09616.

As described therein, agglomerates of finely divided powder medicaments, such as micronized powders having a particle size smaller than 10 μm, can be produced which require no binders. However, they can be formed with excipients. These agglomerates can then be administered through an inhaler for powdered medications.

The ability to create particles without an added binder is significant to inhalation therapy and can pose a great advantage over other techniques which use water or other traditional binders in agglomerate formation. Agglomerates of pure drug can provide great advantages when formulating and handling powders. It has been found, however, that at doses of about 100–500 μg of a drug such as mometasone furoate and below, agglomerates of pure drug can suffer from hang up and dosing variability can be a genuine concern. Even in dosing systems designed to provide relatively larger doses of pharmacologically active agent, such as over 500 μg, the resulting agglomerates of pure drug can still suffer from integrity problems. These agglomerates are still relatively soft and can be crushed during metering thereby providing variability in dosing. The material can also be broken fairly readily by, for example, dropping an inhaler from a height of about four feet. This would prematurely result in the formation of smaller particles which are more difficult to handle. In fact, it is the handling difficulties of the fine drug particles that originally necessitated agglomeration.

If binder-containing agglomerates are to be used, such agglomerates can be made by the methods described in, for example, U.S. Pat. No. 4,161,516 and Great Britain Patent 1,520,247 which disclose the use of certain binding materials, including water, for the production of agglomerates for oral inhalation. According to the processes described therein, prior to agglomeration, the moisture content of certain "self agglomerating" or hygroscopic micronized drugs are elevated. After the micronized powder has been elevated to the desired water content level, it is agglomerated. Non-hygroscopic materials must be bound with more traditional binders as described therein. Similarly, PCT International Publication WO 95/05805 discloses a process for forming agglomerates where a mixture of homogeneous micronized materials is treated with water vapor to eliminate any convertible amorphous content which may destabilize at a later point. After treatment with water vapor, the now crystalline material is agglomerated. However, this application warns that if the vapor exposure is conducted after agglomeration, the product is "useless in an inhalation device."

The effect of moisture on the tableting characteristics of anhydrous lactose is discussed in Sebhatu, Elamin and Ahineck, "Effect of Moisture Sorption on Tableting Characteristics and Spray Dried (15% Amorphous) Lactose," *Pharmaceutics Research*, Vol. 11, No. 9, pp. 1233–1238 (1994). The article does not, however, discuss the formation of agglomerates, or the production of agglomerates which can yield an acceptable "fine particle fraction," also known as a "respirable fraction" when administered as part of oral inhalation therapy.

One particularly important approach to agglomerate formation was disclosed in PCT International Publication WO 98/41193. The invention described therein included a process of producing agglomerates. The process included the steps of providing particles of at least one first material, generally a pharmacologically active agent, and providing particles of at least one solid binder or solid carrier. At least one of these two particles, the drug or the solid binder, included convertible amorphous content. The convertible amorphous content of the binder and/or the drug should be capable of being converted to a crystalline form upon exposure to a pre-selected stimulus which includes, among other things, humidity.

The particles of binder or carrier and drug are then agglomerated while maintaining the convertible amorphous content. After agglomeration is complete, the convertible amorphous content within the agglomerates is exposed to the pre-selected stimulus and is converted to a crystalline form.

Not surprisingly it is very important to the performance of the agglomerates and to the ability to deliver an acceptable fine particle fraction of free particles of the pharmaceutically active materials that the properties of the agglomerate carrier or binder be tightly controlled. It is also important to control the properties of the drug particles. Desirably one would be able to provide not only particles of a specified size, but also a very tight particle size distribution. Ideally, one could coordinately provide a desirable amount of convertible amorphous content. The amorphous content can be critical to the strength, bulk density and/or hardness of the resulting agglomerate. If too little amorphous content is present, then the agglomerates will be insufficiently robust to withstand packaging, shipment and use. If too much amorphous content is provided, then there is a risk that the agglomerate will be too strong and/or hard and that an unacceptable fine particle fraction will be delivered from a powder inhaler. Similarly, the size of the particles and the particle size distribution are critical to accurately formulating the agglomerates to provide an acceptable fine particle fraction and to provide accurate dose delivery uniformity due to consistency of the resulting bulk density. Unfortunately, no processes are known for reproducibly producing particles of drugs and/or solid carriers with accurately controlled particle size distribution and amorphous content. It is to this improvement that the present invention is directed.

SUMMARY OF THE INVENTION

The present invention is directed to a method of producing a particulate substance which is particularly suitable for use in producing agglomerates containing a pharmaceutically active material and preferably a solid binder or solid carrier. The particulate produced by the process is also contemplated. The method includes the steps of micronizing a particulate material from an original particle size to an intermediate particle size in a manner which imparts an increase in the amount of amorphous content of the particulate. Some or all of that imparted amorphous content is convertible amorphous content. The particle size distribution is reduced by this micronizing step. Thereafter, the micronized particulate is "cured" by exposure to a predetermined stimulus such as, for example, exposure to controlled relative humidity at a specified temperature. This curing process is conducted for a time sufficient to reduce at least a portion, and in many instances preferably all, of the amorphous content of the particulate which is convertible when exposed to that particular stimulus. Thereafter, the cured particulate is micronized again wherein the particulate is reduced further in size from the intermediate particulate size to a final particulate size. A desired level of convertible amorphous content is also created by the subsequent micronizing step.

The particulate can be any pharmaceutically acceptable material including a pharmaceutically active material (i.e., a drug) or a non-therapeutically active material such as a solid carrier, solid binder or other pharmaceutical excipient. Indeed, particulate can be composed of both at the same time.

Stated another way, the method of producing a particulate in accordance with the present invention includes the steps of micronizing a particulate material having a first particle size distribution, from that first particle size distribution to intermediate particles having a second particle size distribution. The second particle size distribution is different than the first particle size distribution as the particulate has been made smaller, on average. Micronization is accomplished in a manner which imparts an increase in the amorphous content of the intermediate particulate relative to the starting particulate before the preceding micronization step. The intermediate particulate is then cured to reduce its amorphous content. Finally, the cured intermediate particulate is re-micronized to a third particle size distribution, which is different than the first or second particle size distribution because the particles are again made smaller on average. The re-micronized particulate also have an amount of amorphous content which is greater than that of the cured intermediate particulate. Thus, in a first micronizing step, an amount of amorphous content is imparted to the particles. Curing will reduce an amount of amorphous content which is convertible when exposed to the stimulus. This also reduces the total amorphous content. Thereafter, upon re-micronizing, the particles contain additional amorphous content, preferably convertible amorphous content.

Preferably, the final particle size of particulate solid carrier produced in accordance with this process is at least about 60% by volume less than or equal to 5 μm and its pre-determined convertible amorphous content (as determined by specific heat of crystallization, using techniques described infra) is between about 1 and about 20 Joules/gram ("J/g" or "J/gram"). More preferably, the final particle size of the particulate solid carrier is at least about 70% by volume less than or equal to 5 μm and a pre-determined convertible amorphous content is between about 2 and about 16 Joules/gram. Most preferably, the final particle size of the particulate solid carrier is at least about 80% by volume less than or equal to 5 μm and the pre-determined amorphous content is between about 3.8 and about 7 Joules/gram.

Preferably, the final particle size of particulate pharmaceutically active material produced in accordance with these methods is at least about 60% by volume less than or equal to 5 microns and a pre-determined convertible amorphous content is between about 1 and about 20 Joules/gram. More preferably, the final particle size of the particulate pharmaceutically active material is at least about 80% by volume less than or equal to 5 microns and a pre-determined convertible amorphous content is between about 2 and about 16 Joules/gram. Most preferably, the final particle size of the particulate pharmaceutically active material is at least about 90% by volume less than or equal to 5 microns.

Preferably, when the pharmaceutically acceptable material useful for the formation of an agglomerate treated by these processes is a non-therapeutically active, non-pharmaceutically active material, the pharmaceutically acceptable material can be a common additive or excipient such as lactose (including both hydrous and anhydrous lactose), and the like. However, since the same process can be performed on the pharmaceutically active material as well, the pharmaceutically active material can be agglomerated with either a traditional solid carrier or a solid carrier which has also been produced in accordance with the methods of the present invention. The pharmaceutically active material produced using these methods will have both controlled particle size distribution and controlled amorphous content and can also be used to form agglomerates without an additional solid carrier and/or with another pharmaceutically active agent, one treated by this method or otherwise.

The present invention also relates to an agglomerate produced by agglomerating a pharmaceutically active substance and/or solid carrier particles at least one of which has been produced in accordance with the present invention.

DETAILED DESCRIPTION OF THE PREFERRED EMBODIMENTS

In accordance with the present invention, the term "pharmaceutically acceptable material" can include either pharmaceutically active materials or non-pharmaceutically active materials. Pharmaceutically active materials are drugs, vitamins, minerals, herbs, dietary supplements and the like, which produce a therapeutic benefit when administered to a patient in need thereof. Non-pharmaceutically active materials can include, inter alia, solid carriers, solid binders and other traditional, pharmaceutically acceptable excipients which generally do not exhibit a therapeutic benefit to a patient when administered as part of a dosage form. An "agglomerate," in accordance with the present invention, generally means an amalgamation of smaller particles to form larger particles. These smaller particles can be held together by traditional binders or by crystallizing the convertible amorphous content imparted to a particle by the processes of the present invention. "Amorphous content" as used herein, refers to a portion of at least the surface of a particle of a pharmaceutically acceptable material which is non-crystalline. "Convertible amorphous content" refers to that portion of the amorphous content of a pharmaceutically acceptable material which, upon exposure to a predetermined stimulus, can be converted from an amorphous form to a crystalline form. The amount of convertible amorphous content desired may depend on a number of factors relating to the specifics of the agglomerates contemplated and the degree and manner of processing. The amount of convertible amorphous content is also related to the stimulus used. A particulate produced in accordance with the present invention may have a greater amount of convertible amorphous content relative to one stimulus than relative to another. Therefore, the desired convertible amorphous content can dictate the degree of processing and/or the stimulus used. A drug might have too much convertible amorphous content if a first stimulus is used, but the desired level of convertible amorphous content if some other stimulus is used.

Convertible amorphous content can be measured by known methods, such as X-ray powder diffraction, differential scanning calorimetry, solution calorimetry and others. These can more preferably include isothermal microcalorimetry, such as by the use of a Thermometrics 2277 Thermal Activity Monitor (Thermometrics AB, Sweden) where convertible amorphous content can be quantified in terms of Joules/gram by measuring the specific heat of crystallization of that particulate. Using techniques offered by the manufacturer, a known quantity of material having amorphous content is exposed to an environment of about 38% relative humidity ("RH"), generated by a saturated solution of sodium iodide, at 25° C. and the heat evolved is plotted against time.

The heat of crystallization thus measured is the total heat evolved by an amount of a particulate, having convertible amorphous content, during the entire crystallization process. This total heat evolved can include not only that heat evolved during the transition from amorphous form to crystalline form, but also, where applicable, the heat evolved during moisture absorption before the transition.

Thus, the convertible amorphous content of a particulate corresponds to the heat of crystallization of the particulate when exposed to a specific stimulus, measured in Joules/gram. The higher the relative heat of crystallization, the higher the degree of convertible amorphous content. For anhydrous lactose, about 45 Joules/gram roughly equals 100% amorphous content. A measured heat of 3.2–6 Joules/gram roughly equates to between about 7 and about 13% amorphous content.

The "stimulus," as used herein, is preferably humidity. However, other stimuli can include, without limitation, temperature, solvent vapor and the like. When humidity is used, the relative humidity and length of exposure should be coordinated to provide a desired degree of conversion of the convertible amorphous content.

Agglomerates produced in accordance with the present invention can be made from a plurality of particles of at least one pharmaceutically acceptable material prepared in accordance with the present invention, with or without other particulates or excipients. Where, for example, the pharmaceutically acceptable material treated in accordance with the present invention is a pharmaceutically active material or drug, it is not necessary that any of the other materials used in agglomerate formation contain convertible amorphous content. However, there may be an advantage to using one or more different types of particles, all of which have been produced in accordance with the present invention and therefore all have a controlled particle size distribution and convertible amorphous content.

It is also possible in accordance with the present invention to produce an agglomerate of a pharmaceutically active material produced in accordance with the present invention with no other binder or excipient. In addition, where a first pharmaceutically active material is treated in accordance with the present invention to provide a specified particle size distribution and a convertible amorphous content, it can be agglomerated with a second drug, one which has not been treated in accordance with the present invention. The first drug can, in essence, function as a solid binder/carrier.

Agglomerates can be used in a formation of a tablet, capsule or other traditional dosage form or they can be administered directly, such as in oral inhalation therapy. Agglomerates can be produced in any known manner, but preferably, they are produced by the techniques described in PCT International Publication WO 98/41193, the text of which is hereby incorporated by reference. This process is generally described in the foregoing introductory section.

A "solid carrier" in accordance with the present invention is an excipient with which a drug or pharmaceutically active material can be agglomerated. The solid carrier may act as a solid binder where, for example, one seeks to capitalize on the convertible amorphous content imparted to the solid carrier and its subsequent conversion to crystalline form as a means of binding the agglomerate particles. If a traditional binding system is used, or if the drug will provide the total convertible amorphous content, the more generic term, "solid carrier," is more appropriate.

Particles of solid carrier in accordance with the present invention, preferably will be produced such that they have a pre-determined convertible amorphous content ranging from between about 1 to about 20 Joules/gram and a particle size distribution of at least 60% by volume less than or equal to 5 μm. More preferably, the particles of solid carrier will have a pre-determined convertible amorphous content ranging from between about 2 to about 16 Joules/gram and a particle size distribution of at least 70% by volume less than or equal to 5 μm. Most preferably, the particles of solid carrier will have a pre-determined convertible amorphous content ranging from between about 3.8 to about 7 Joules/gram and a particle size distribution of at least 80% by volume less than or equal to 5 μm.

These same ranges of convertible amorphous content and particle size distribution can also apply to particles of a pharmaceutically active material. However, preferably the particle size distribution for pharmaceutically active materials is finer than for solid carriers. Preferably, particles of pharmaceutically active materials produces in accordance with the present invention will have an particle size distribution of about 80% by volume less than or equal to 5 μm. More preferably, the drug component will have an particle size distribution of at least 90% by volume less than or equal to 5 μm.

Note that when particles having a specified convertible amorphous content and particle size distribution are mixed with other particles having a different convertible amorphous content and particle size distribution, the convertible amorphous content and particle size distribution for the system will change proportionally. Particle size and particle size distribution can be determined by any of the many techniques known and used in industry. These can include the use of a Sympatec HELOS Laser Diffraction Particle Size Analyzer with a RODOS Dry Powder Disperser, using standard techniques provided by the manufacturer. This device is available from Sympatec, Inc. of Princeton, N.J. USA.

When an agglomerate is formed from pharmaceutically acceptable particulate material including both a drug and a solid carrier which have been treated in accordance with the present invention, it is not a requirement that both particulates fall within the ranges of particle size distribution and convertible amorphous content discussed above. However, it may be desirable that both meet the described standards.

The pharmaceutically acceptable material in accordance with the present invention can include solid carriers/solid binders such as, without limitation, non-therapeutically active materials including polyhydroxy aldehydes, polyhydroxy ketones, and amino acids. Preferred polyhydroxy aldehydes and polyhydroxy ketones are hydrated and anhydrous saccharides including, without limitation, lactose, glucose, fructose, galactose, trehalose, sucrose, maltose, raffinose, mannitol, melezitose, starch, xylitol, mannitol, myoinositol, their derivatives, and the like. Lactose is preferred.

Pharmaceutically active materials contemplated for use in accordance with the present invention include, for example, drugs, vitamins, herbs, natural products, dietary supplements and the like. Particularly preferred pharmaceutically active materials in accordance with the present invention include, without limitation, corticosteroids such as mometasone furoate, beclomethasone dipropionate, budesonide, fluticasone, dexamethasone, flunisolide, triamcinolone, (22R)-6α,9α-difluoro-11β, 21-dihydroxy-16α, 17α-propylmethylenedioxy-4-pregnen-3,20-dione, tipredane and the like. β-agonists (including $\beta_1$ and $\beta_2$-agonists) including, without limitation, salbutamol (albuterol), terbutaline, salmeterol and bitolterol may also be used. Formoterol (also called "eformoterol"), e.g. as the fumarate or tartrate, a highly selective long-lasting $\beta_2$-adrenergic agonist having bronchospasmolytic effect, is useful. Another β-agonist which can be used in accordance with the present invention is (2(1H)-Quinolinone,8-hydroxy-5-[1-hydroxy-2-[[2-(4-(methoxyphenyl)-1methylethyl]amino] ethyl]-monohydrochloride, also identified by Chemical Abstract Number CAS-137888-1 1-0, disclosed in U.S. Pat. No. 4,579,854, the text of which is hereby incorporated by reference. Anticholinergics such as tiotropium bromide, ipratropium bromide and oxitropium bromide may be used. So too can sodium cromoglycate, nedocromil sodium and leukotriene antagonists such as montelukast, zafirlukast and pranlukast. Bambuterol, e.g. as the hydrochloride, fenoterol, e.g. as the hydrobromide, clenbuterol, e.g. as the hydrochloride, procaterol, e.g. as the hydrochloride, and broxaterol are highly selective $\beta_2$-adrenergic agonists can be used in the invention. Several of these compounds could be administered in the form of pharmacologically acceptable esters, salts, solvates, such as hydrates, or solvates of such esters or salts, if any. Both racemic mixtures as well as one or more optical isomers are also contemplated. The drug in accordance with the present invention can also be an inhalable protein or a peptide such as insulin, interferons, calcitonins, parathyroid hormones, granulocyte colony-stimulating factor and the like. Combinations of these, such as a combination of a corticosteroid and a $\beta$-agonist, are also contemplated. A particularly preferred pharmacologically active agent in accordance with the present invention is mometasone furoate.

If one attempts to use a single stage micronization process either on a drug or a solid carrier (or both), it is difficult to reproducibly achieve both a desired level of convertible amorphous content and a desired particle size distribution. This is particularly true in a production setting where batch after batch of processed materials are required. Longer exposure in a micronizer yields finer particles but higher amorphous content. Shorter exposures may provide the correct amorphous content but not necessarily the desired particle size distribution.

For example, Table 1 provides data from micronizing anhydrous lactose using a single-stage micronization process and a MICRON-MASTER™ 4 inch (100 cm) diameter Jet Pulverizer, available from the Jet Pulverizer Co. of Palmyra, N.J. USA. In this device, a stream of powdered feed material is impinged by a high-pressure gas stream as it enters a chamber having rounded walls; particles undergo numerous collisions with each other and the walls to produce size reductions before the particles reach the chamber exit. Gas pressure [expressed herein in both pounds per square inch gauge (psig) and Newtons per square meter (N/m$^2$) units] and powder feed rate are the principal parameters affecting final particle sizes.

TABLE 1

| BATCH NO. | GAS PRESSURE, psig (N/m$^2$) | FEED-RATE (g/min) | SPEC. HEAT OF CRYSTAL. (J/g) | VOL. % PARTICLE SIZE <5 μm |
|---|---|---|---|---|
| 06 | 100 (6.9E5)* | 50 | 12.5 | 93.9 |
| 07 | 80 (5.5E5) | 50 | 10.8 | 88.6 |
| 08 | 100 (6.9E5) | 50 | 13.6 | 91.1 |
| 09 | 80 (5.5E5) | 50 | 11.6 | 88.7 |
| 10 | 80 (5.5E5) | 75 | 6.9 | 78.6 |
| 11 | 80 (5.5E5) | 100 | 4.8 | 72.8 |
| 12 | 80 (5.5E5) | 100 | 5.7 | 71.8 |
| 13 | 80 (5.5E5) | 50 | 10.8 | 87.6 |
| 14 | 80 (5.5E5) | 50 | 13.2 | 85.8 |
| 15 | 80 (5.5E5) | 50 | 11.8 | 84.0 |
| 16 | 80 (5.5E5) | 50 | 12.3 | 87.5 |
| 17 | 100 (6.9E5) | 75 | 11.9 | 86.3 |
| 18 | 100 (6.9E5) | 100 | 9.9 | 80.9 |
| TARGET RANGE | | | 3.8–7 | >80% |

* "E" indicates an exponent of ten, e.g., 6.9E5 = 6.9 · 10$^5$. This nomenclature will be used in data presentation throughout the specification.

Of the thirteen batches identified in Table 1, only batches 10,11 and 12 were outside the target particle size range. However, only batches 10,11 and 12 had acceptable levels of specific heat of crystallization (a measure of convertible amorphous content). Therefore, it is difficult to reliably achieve both the desired range of amorphous content and the desired particle size distribution by the use of single stage micronization process, particularly from batch to batch. The present invention solves this problem by breaking the micronization process into at least two individual steps. In the first step, particulate material is micronized to a predetermined intermediate particle size distribution. In the micronizing process, a certain level of amorphous content is imparted.

If these intermediate particles were then immediately re-introduced to a micronizer, their particle sizes might be reduced to acceptable levels. However, the degree of amorphous content imparted would become unacceptably high. Note that in table 1 all of the batches which had acceptable particle size distribution had a degree of specific heat of crystallization (i.e. amorphous content) which was higher than desired.

"Particle size distribution" or desired particle size distribution should be understood to mean that the particle size falls within a range wherein at least a specified percentage of a batch of particles has a maximum specified size when measured by volume. The terms "micronize," "micronization" and "micronizing" should be understood to encompass any process which results in a desired level of particle size reduction. It should be understood that while micronization was accomplished herein using a jet pulverizer, any other device which can provide the desired particle size distribution and impart a certain amount of amorphous content can also be used. Indeed, this can be accomplished using other traditional microparticle generating devices such as milling, spray drying or ball milling. See Briggner, Buckton, Bystrom and Darcy, "The Use of Isothermal Microcalorimetry in the Study of Changes in Crystallinity Induced During the Processing of Powders," *International Journal of Pharmaceutics*, Vol. 105, pp. 125–135 (1994).

The methods of the present invention interject a "curing" step between at least two micronizing steps. By subjecting the intermediate particulate to a stimulus such as, in the examples described herein, subjecting anhydrous lactose to relative humidity of between 35 and 45% at 20–25° C. for a suitable period of time of at least about 4 hours (while the particulate is in layer or cake of material approximately 5 cm thick), one can reduce, if not eliminate, the convertible amorphous content imparted in the first micronization step. By then re-micronizing the intermediate particulate, once the amorphous content has been recrystallized, in whole or in part, the degree of additional amorphous content imparted in the subsequent micronization step can be controlled to fall within the desired parameters while the particle size and particle size distribution are adjusted to acceptable levels.

The specifics of this process can vary significantly. For example, the micronization will generally occur in two steps with a single curing step between each micronization step. However, micronization can occur in three or more steps and there may or may not be a curing step between each successive micronization. Similarly, the curing steps may vary widely depending upon a number of variables, some of which may change from step to step. The specifics of the curing steps may vary as to duration of exposure, type of stimulus, temperature, the thickness of the cake and the degree of amorphous content left when the exposure is discontinued, and the like. Changing the identity of the material being processed also may alter certain process conditions; for example, curing lactose monohydrate particles may require the use of higher humidity conditions (e.g., 50–55 % relative humidity) than those used to cure anhydrous lactose.

As shown in Table 2, a set of nine anhydrous lactose micronization experiments was performed using the present invention. The micronization gas pressure was fixed at 80 psig (5.5·10$^5$ N/m$^2$).

TABLE 2

| 1st Stage Micronization | | | | After Curing | 2nd Stage Micronization | | | |
|---|---|---|---|---|---|---|---|---|
| Batch No. | Gas Pressure/ Feed Rate psig/(g/min) | Vol. % Particle Size <5 μm | Spec. Heat Of Crystal. (J/g) | Vol. % Particle Size <5 μm | Batch No. | Gas Pressure/ Feed Rate psig/(g/min) | Spec. Heat Of Crystal. (J/g) | Vol. % Particle Size <5 μm |
| 19 | 80*/100 | 67.2 | 0 | 68.2 | 19-A | 80*/50 | 9.9 | 95.8 |
|  |  |  |  |  | 19-B | 80*/75 | 7.3 | 93.0 |
|  |  |  |  |  | 19-C | 80*/100 | 5.4 | 89.6 |
| 20 | 80*/200 | 51.9 | 0 | 52.4 | 20-A | 80*/50 | 9.6 | 92.3 |
|  |  |  |  |  | 20-B | 80*/75 | 6.2 | 84.2 |
|  |  |  |  |  | 20-C | 80*/100 | 5.5 | 83.3 |
| 21 | 80*/300 | 47.0 | 0 | 47.2 | 21-A | 80*/50 | 10.7 | 91.9 |
|  |  |  |  |  | 21-B | 80*/75 | 7.5 | 84.4 |
|  |  |  |  |  | 21-C | 80*/100 | 6.6 | 84.4 |
| TARGET RANGE | | | | | | | 3.8–7 | >80% |

* $5.5 \cdot 10^5$ N/m$^2$

In the first stage of micronization, particles attained a size distribution of between about 47 and about 67% by volume less than or equal to 5 μm. Thereafter, the particles were placed in trays in layers of about 5 cm thick and exposed to 35–45% RH at a temperature of between about 20–25° C. for at least about 4 hours until the specific heat of crystallization went to about zero. This indicated that no more convertible amorphous content existed and that, with the exception of non-convertible amorphous content, the entire particulate was completely crystalline in nature. Thereafter, each of the batches were micronized in a second stage using various feed rates, as specified. All of the batches of solid carrier processed in the second stage of micronization had a particle size distribution of greater than or equal to 80% by volume less than or equal to 5 μm. Thus all were acceptable in accordance with a particularly preferred aspect of the present invention. Most of the batches also had a specific heat of crystallization falling within about 3.8 to about 7 Joules/gram.

To verify these results, an additional twenty-three batches of micronized anhydrous lactose were prepared by the methods described herein, with the objective of preparing particles having heats of crystallization between 3.8 and 7 J/g (See Table 2, Batch No. 19C). The results are illustrated in Tables 3 and 4.

TABLE 3

| BATCH NO. | Specific Heat of Crystallization (J/g) | Batch Size (kg) |
|---|---|---|
| 2007 | 5.2 | 15 |
| 2006 | 4.7 | 15 |
| 2005 | 5.2 | 15 |
| 2004 | 4.8 | 15 |
| LAC-14 | 4.6 | 15 |
| LAC-13 | 4.8 | 15 |
| LAC-12 | 5.0 | 15 |
| LAC-11 | 6.6 | 15 |
| LAC-10 | 4.6 | 15 |
| LAC-09 | 4.7 | 30 |
| LAC-08 | 5.4 | 15 |
| LAC-07 | 5.4 | 15 |
| LAC-06 | 3.9 | 15 |
| LAC-05 | 4.1 | 15 |
| LAC-04 | 5.7 | 30 |
| LAC-03 | 5.0 | 30 |
| LAC-02 | 5.3 | 30 |
| LAC-01-C | 4.4 | 2 |
| LAC-27-A | 5.6 | 45 |
| LAC-26-C | 5.2 | 4.8 |
| LAC-24-A | 5.6 | 15 |
| LAC-23-A | 5.7 | 15 |
| LAC-22-A | 6.5 | 15 |
| RANGE | 3.9–6.6 |  |

TABLE 4

| | PARTICLES | | | | |
|---|---|---|---|---|---|
| BATCH | Vol. % <1 μm | Vol. % <3 μm | Vol. % <5 μm | Vol. % <10 μm | MEDIAN μm |
| 2007 | 26.9 | 66.7 | 86.5 | 98.7 | 2.0 |
| 2006 | 28.2 | 68.2 | 88.2 | 99.3 | 1.9 |
| 2005 | 28.3 | 68.8 | 88.7 | 99.3 | 1.9 |
| 2004 | 28.6 | 68.9 | 88.5 | 98.9 | 1.9 |
| LAC-14 | 25.9 | 67.4 | 88.4 | 99.5 | 2.0 |
| LAC-13 | 25.9 | 67.4 | 88.6 | 99.5 | 2.0 |
| LAC-12 | 28.8 | 73.7 | 92.3 | 99.7 | 1.8 |
| LAC-11 | 29.1 | 74.5 | 92.6 | 99.7 | 1.7 |
| LAC-10 | 27.3 | 71.2 | 90.9 | 99.6 | 1.9 |
| LAC-09 | 25.3 | 64.9 | 85.5 | 98.6 | 2.1 |
| LAC-08 | 26.3 | 68.9 | 89.7 | 99.5 | 2.0 |
| LAC-07 | 26.4 | 69.0 | 89.2 | 99.4 | 1.9 |
| LAC-06 | 24.6 | 66.2 | 87.7 | 99.4 | 2.1 |
| LAC-05 | 25.8 | 69.3 | 89.8 | 99.5 | 2.0 |
| LAC-04 | 28.4 | 72.0 | 91.2 | 99.7 | 1.8 |
| LAC-03 | 25.7 | 66.1 | 87.3 | 99.4 | 2.1 |
| LAC-02 | 25.6 | 65.5 | 86.7 | 99.1 | 2.1 |
| LAC-01-C | 24.8 | 64.0 | 84.8 | 98.9 | 2.1 |
| LAC-27-A | 26.2 | 67.3 | 87.9 | 99.3 | 2.0 |
| LAC-26-C | 28.4 | 73.3 | 92.5 | 99.8 | 1.8 |
| LAC-24-A | 26.5 | 75.0 | 93.1 | 99.9 | 1.7 |
| LAC-23-A | 25.3 | 71.8 | 90.8 | 99.6 | 1.8 |
| LAC-22-A | 29.5 | 73.6 | 92.3 | 99.7 | 1.7 |
| RANGE | 24.6–29.5 | 64.0–75.8 | 84.8–93.8 | 98.6–99.9 | 1.7–2.1 |
| TARGET | >20% | >60% | >80% | >95% | 1.5–2.5 |

As shown in Table 3, the specific heat of crystallization of each of the batches fell between 3.9 and 6.6 Joules/gram, i.e., within the most preferred ranges in accordance with the present invention. As shown in Table 4, each of the batches included a particle size distribution wherein greater than 80% by volume of the particles were less than 5 μm in size. Indeed, over the entire twenty-three batches, the particle size distributions ranged from 84.8 to 93.8% by volume of particles less 10 than 5 μm. Substantially all of the particulate was less than 10 μm in size.

As previously noted, in certain circumstances it may be desirable to process both the drug and the carrier together. For example, it may be desirable to undertake a first micronization step with the carrier of anhydrous lactose alone. After curing, final micronization can take place with both the drug and the intermediate particulate, depending on the relative particle sizes desired. It is also possible to process both drug and carrier in the same micronization steps at the same time.

For this reason, it may be desirable to produce agglomerates in accordance with the present invention in which merely the drug is processed in accordance with the present invention. Agglomerates can then be formed of the drug itself, alone or the drug and a solid carrier. The solid carrier may or may not have a convertible amorphous content and may or may not have also been processed in accordance with the invention. Alternatively, by imparting certain particle size distribution and convertible amorphous content to the drug, another drug, one not including convertible amorphous content, may be used in place of a solid carrier.

It should be understood that while there may objectively be an absolute level of amorphous content for a given particle, the amount of convertible amorphous content may be the same or different and may be a function of the converting stimulus to be applied. Relative to humidity, a drug may have no convertible amorphous content. Relative to some other stimulus, such as an alcohol, however, it may contain a significant quantity of convertible amorphous content. In preferred embodiments, the amount of convertible amorphous content is relative to humidity as a stimulus.

The generally preferred stimulus in accordance with the present invention is humidity. When using humidity, the higher the level of humidity, at a given temperature, the less the amount of time necessary for exposure. However, a somewhat gradual and controlled conversion is preferred. Particles containing convertible amorphous content can be exposed to relative humidity of between about 30% and about 80% (at 25° C.) for a time period which is sufficient to convert the entire amorphous content. More preferably, the convertible amorphous content is converted by exposure to an atmosphere having a water content equal to a relative humidity of between about 35% and about 60% (measuring the relative humidity at about 25° C. This is particularly useful when the solid carrier is anhydrous such as anhydrous lactose. The amount of time can vary dramatically with the size and density of the particles and the surface area of exposure. For example, placing a thin layer of particles on a flat open tray will yield a much faster conversion overall than placing the same quantity of particles in a narrow container. In certain cases, the length of exposure need be on the order of tens of minutes. In other instances, one to two days may be required.

Because, preferably for anhydrous lactose, the exposure is controlled to relative humidities of 65% or below (at 25° C.), there is relatively little concern about overexposure. So long as sufficient time is provided to allow all of the convertible amorphous content of the particles to convert to crystalline form, the fact that additional exposure may take place is generally not of any consequence. If humidity levels above about 65% are used, however, then the water vapor could actually act as a binder.

A presently preferred formulation in accordance with the present invention is a mixture of mometasone furoate with anhydrous lactose which has been processed in accordance with the present invention. The mometasone furoate preferably has an particle size distribution of at least about 80% by volume less than or equal to 5 μm and more preferably at least about 90% by volume less than or equal to 5 μm. The anhydrous lactose has a particle size distribution of at least about 70% by volume less than or equal 5 μm and a convertible amorphous content (based on humidity as the stimulus) of between about 3.8 and about 7 Joules/gram. More preferably, these two components are mixed in a ratio of 10:1–1:100 parts of mometasone furoate to parts of anhydrous lactose. Most preferably, the particles are provided in an amount of 1 part mometasone furoate to about 5.8 parts anhydrous lactose. When so mixed, the amount of convertible amorphous content for the system is 3.2–6 Joules/gram. Thus, while the ranges of convertible amorphous content reported for a particular particulate are accurate, they will vary when mixed with other materials depending upon the relevant ratios.

Of course, pharmaceutically active materials having a particle size distribution of at least 80% by volume less than or equal to 5 μm and more preferably at least 90% by volume less than or equal to 5 μm produced in accordance with the present invention are also more generally contemplated. Non-pharmaceutically active materials useful as solid carriers are contemplated preferably having an particle size distribution of at least 70% by volume less than or equal to 5 μm and having a convertible amorphous content of between about 1 and about 20 Joules/gram. More preferably, these particles of solid carrier, produced by the methods of the invention, will have an amount of convertible amorphous content ranging from between about 2 and about 16 Joules/gram and most preferably between about 3.8 and about 7 Joules/gram. Mixtures wherein the particulate of the pharmaceutically active material has an particle size distribution of at least 80% by volume less than or equal to 5 μm, and more preferably at least about 90% by volume less than or equal to 5 μm and solid carriers having a particle size distribution of at least about 70% by volume less than or equal to 5 μm are specifically contemplated. The amount of convertible amorphous content for the mixed particulate should range from between about 2 to about 16 Joules/gram and more preferably 3.2 to 6 Joules/gram.

We claim:

1. A method of producing a particulate substance, comprising the steps of: micronizing a particulate material having a first particle size distribution to form intermediate particles having a second particle size distribution which is smaller than said first particle size distribution, in a manner which results in said intermediate particles having an increased amorphous content; curing said intermediate particles to reduce the amorphous content thereof; and re-micronizing said cured intermediate particles to form particles having a third particle size distribution, which is smaller than said second particle size distribution, and an amorphous content greater than that of said cured intermediate particles.

2. The method of claim 1 wherein said re-micronized particles are a solid carrier having a particle size distribution of at least about 60% by volume less than or equal to about 5 μm and a predetermined convertible amorphous content corresponding to a heat of crystallization of between about 1 and about 20 Joules/gram.

3. A particulate substance produced by the process of claim 2.

4. The method of claim 1 wherein said re-micronized particles comprise a solid carrier having a particle size distribution of at least about 70% by volume less than or equal to about 5 μm and a predetermined convertible amorphous content corresponding to a heat of crystallization of between about 2 and about 16 Joules/gram.

5. A particulate substance produced by the process of claim 4.

6. The method of claim 1 wherein said re-micronized particles comprise a solid carrier having a particle size distribution of at least about 80% by volume less than or equal to about 5 μm and a predetermined convertible amorphous content corresponding to a heat of crystallization of between about 3.8 and about 7 Joules/gram.

7. The method of claim 6 wherein said particulate material comprises lactose.

8. A particulate substance produced by the process of claim 6.

9. The method of claim 1 wherein said particulate material comprises lactose.

10. The method of claim 1 wherein said particulate material comprises a pharmaceutically active-material and said particulate substance has a particle size distribution of at least about 80% by volume less than or equal to about 5 μm and a predetermined amorphous content corresponding to a heat of crystallization between about 1 and about 20 Joules/gram.

11. The method of claim 10, wherein the pharmaceutically active material comprises mometasone furoate.

12. The method of claim 10, wherein the pharmaceutically active material comprises a salt of eformoterol.

13. A particulate substance produced by the process of claim 10.

14. A particulate substance produced by the process of claim 1.

15. A particle mixture comprising: a particulate solid carrier having a particle size distribution of at least 70% by volume less than or equal to 5 μm; and particles of mometasone furoate having a particle size distribution of at least about 80% by volume less than or equal to 5 μm; wherein the total amount of convertible amorphous content for said particle mixture corresponds to a heat of crystallization ranging from about 3.2 to about 6 Joules/gram.

16. The particle mixture of claim 15 wherein said mometasone furoate particles have a particle size distribution of at least 90% by volume less than or equal to 5 μm.

17. A particle mixture comprising: a particulate solid carrier having a particle size distribution of at least 70% by, volume less than or equal to 5 μm; and particles of a pharmaceutically active material having a particle size distribution of at least about 80% by volume less than or equal to 5 μm; wherein the total amount of convertible amorphous content for said particle mixture corresponds to a heat of crystallization ranging from about 2 to about 16 Joules/gram.

18. The particle mixture of claim 17 wherein said mometasone furoate particles have a particle size distribution of at least 90% by volume less than or equal to 5 μm.

19. A particle mixture comprising: a particulate solid carrier having a particle size distribution of at least 70% by volume less than or equal to 5 μm; and particles of an eformoterol salt having a particle size distribution of at least about 80% by volume less than or equal to 5 μm; wherein the total amount of convertible amorphous content for said solid particle mixture corresponds to a heat of crystallization ranging from about 2 to about 16 Joules/gram.

20. The particle mixture of claim 19 wherein said eformoterol salt particles have a particle size distribution of at least 90% by volume less than or equal to 5 μm.

21. A particle mixture comprising: a particulate solid carrier having a particle size distribution of at least 70% by volume less than or equal to 5 μm; and particles of a drug selected from the group consisting of mometasone furoate, an eformoterol salt and combinations thereof and having a particle size distribution of at least about 80% by volume less than or equal to 5 μm; wherein the total amount of convertible amorphous content for said particle mixture corresponds to a heat of crystallization ranging from about 2 to about 16 Joules/gram.

22. The particle mixture of claim 21 wherein said drug particles have a particle size distribution of at least 90% by volume less than or equal to 5 μm.

\* \* \* \* \*